(12) United States Patent
Borodic

(10) Patent No.: US 8,926,991 B2
(45) Date of Patent: Jan. 6, 2015

(54) BOTULINUM TOXIN AND THE TREATMENT OF PRIMARY DISORDERS OF MOOD AND AFFECT

(75) Inventor: Gary E. Borodic, Canton, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 869 days.

(21) Appl. No.: 11/447,984

(22) Filed: Jun. 7, 2006

(65) Prior Publication Data

US 2007/0009555 A1   Jan. 11, 2007

Related U.S. Application Data

(60) Provisional application No. 60/690,162, filed on Jun. 14, 2005, provisional application No. 60/693,771, filed on Jun. 27, 2005, provisional application No. 60/721,060, filed on Sep. 28, 2005, provisional application No. 60/738,981, filed on Nov. 23, 2005.

(51) Int. Cl.
*A61K 39/08* (2006.01)

(52) U.S. Cl.
USPC ........................................ 424/239.1; 514/923

(58) Field of Classification Search
None
See application file for complete search history.

(56) References Cited

U.S. PATENT DOCUMENTS

2003/0211121 A1   11/2003   Donovan

FOREIGN PATENT DOCUMENTS

| DE | 19856897 | 6/2000 |
|---|---|---|
| DE | 101 50 415 A1 | 5/2003 |
| WO | WO 01/78760 A2 | 10/2001 |
| WO | 2003063898 | 7/2003 |
| WO | 2004096269 | 11/2004 |
| WO | WO 2005/084705 A | 9/2005 |

OTHER PUBLICATIONS

Setler. Clin J Pain 18: S119-S124, 2002.*
Aguggia et al. Neurol Sci 29: S137-S139, 2008.*
Papapetropoulos et al. Semin Neurol 27: 183-194, 2007.*
Gupta, Pain Med 7: 386-394, 2006.*
Kumar, Ind J Chest Dis All Sci 50: 129-135, 2008.*
Bhat Ex Opin Pharmacother 9: 1721-1733, 2008.*
Biondi, Dental clin North Amer 45: 685-700, 2001.*
Gundersen Prog Neurobiol 14: 99-119, 1980.*
Blumenfeld, Headache 42: 420, Abstract F20, 2002.*
Dobs et al. J Clin Endo Metab 84: 3469-3478, 1999.*
Espana et al Sleep 34: 845-858, 2011.*
Gillette et al Cell Tiss Res 309: 99-107, 2002.*
Lu et al Chest 130: 1915-1923, 2006.*
Caleo et al Toxicon 54: 593-599, 2009.*
Pauly and Horseman Brain Res 348: 163-167, 1985.*
Partial International Search for PCT/US2006/022157 dated Nov. 8, 2006.
Finzi, E. et al., "Treatment of depression with botulinum toxin A: A case series", Dermatologic Surgery 2006 United Kingdom, vol. 32, No. 5, 2006, p. 645-650.
Murry, Thomas, et al., "Spasmodic dysphonia: Emotional status and botulinum toxin treatment", Archives of Otolaryngology Head and Neck Surgery, vol. 120, No. 3, 1994, p. 310-316.
European Search Report dated Sep. 18, 2010, for European Patent Application No. 10003746.4.
U. Kern et al., "Botulinum-Toxin-A in der Behandlung von Phantomschmerzen", Schmerz 2003—17:117-124.
Virgilio Gerald H. Evidente et al., "Case Studies in Movement Disorders", Seminars in Neurology, vol. 23, No. 3, 2003.
David M. Biondi, Do, Headaches and Their Relationship to Sleep:, Dental Clinics of North America, vol. 45, No. 4, Oct. 2001.

* cited by examiner

*Primary Examiner* — Daniel E Kolker
*Assistant Examiner* — Aditi Dutt
(74) *Attorney, Agent, or Firm* — Milbank, Tweed, Hadley & McCloy LLP

(57) ABSTRACT

The invention provides methods for treating primary disorders of mood and affect, including depressive disorders, anxiety and sleep disorders and CNS disorders comprising the administration of a neurotoxin.

19 Claims, 1 Drawing Sheet
(1 of 1 Drawing Sheet(s) Filed in Color)

Glutamate Receptor Activity Botulinum Toxin

Neostriatum Botox-treated Mouse

Neostriatum Untreated Mouse

BOTULINUM TOXIN AND THE TREATMENT OF PRIMARY DISORDERS OF MOOD AND AFFECT

This application claims benefit to U.S. Provisional Application Ser. No. 60/690,162, filed on Jun. 14, 2005; U.S. Provisional Application Ser. No. 60/693,771, filed on Jun. 27, 2005; U.S. Provisional Application Ser. No. 60/721,060, filed on Sep. 28, 2005; U.S. Provisional Application Ser. No. 60/738,981, filed on Nov. 23, 2005, all of which are hereby incorporated herein by reference in their entireties.

FIELD OF THE INVENTION

The present invention relates to the treatment of primary disorders of mood and affect with a neurotoxin, including depressive, anxiety and sleep disorders as well as other CNS disorders.

BACKGROUND OF THE INVENTION

Depression is one of the most prevalent and pervasive forms of mental illness that affects individuals across age and gender lines. (Gainotti et al. (2001) *J. Neural Neurosurg. Psychiatr.* 71: 258-261; Wong et al. (2001) *Nature Rev. Neurosci.* 2: 343-351; Nestler et al. (2002) *Neuron* 34: 13-25). The lifetime risk of major depression is about 12% in men and about 25% in women, generally, (Kessler et al. (1994) *Arch. Gen. Psychiatry* 51: 8). In addition, about 5 to 10% of all patients in the primary care environment, present with major depression, whereas about 3 to 5% of patients are diagnosed with dysthymia. (Barrett et al. (1988) *Arch. Gen. Psychiatry* 45: 1100). In an in-patient setting, however, between 10 and 14% of all patients are diagnosed with major depression. (Blackburn et al. (1997) *Br. J. Psychiatry* 171: 328). Major depression is a particularly disabling and pernicious, in part, because it is recurring. The rate of relapse for patients with major depression is about 40% over a two-year period after a first episode. The occurrence of relapse increases to about 75% within a five year period after the diagnosis of a second episode of major depression. (Solomon et al. (2000) *Am. J. Psychiatry* 157: 229).

Depressive disorders are most commonly treated with three main classes of compounds: 1) monamine oxidase inhibitors; 2) heterocyclic antidepressants; and 3) selective serotonin reuptake inhibitors (SSRIs). The known and currently prescribed antidepressants are by numerous side effects. Monoamine oxidase inhibitors were the first class of antidepressants used clinically. Monoamine oxidase inhibitors, including isocarboxazid, pheneizine, and tranylcypromine, inhibit the metabolism of phenylethylamine and catabolism of dopamine, serotonin and norepinephrine. As a consequence of numerous dietary restrictions associated with the use of monoamine oxidase inhibitors, extensive side effects, including hypertension, headache, myoclonic jerk, sleep disruption, and gastrointestinal complications, monoamine oxidase inhibitors are currently not used as a first-line antidepressant. The tricyclic antidepressants, including, imipramine, desipramine, nortrypline, amitrypline, doxepin and protrypline, produce a variety of anticholinergic side effects, drowsiness, orthostatic hypotension, cardiac arrhythmias and weight gain. Although generally milder than the monoamine oxidase inhibitors and the tricyclic antidepressants, SSRIs also produce numerous side effects. For example, SSRIs, including fluoxetine, paroxetine, fluvoxamine, sertraline, and citalopram, are associated with gastrointestinal distress, jitteriness, agitation and sleep disruption.

In addition to the numerous side effects associated with traditional antidepressant medications, these therapeutics are also characterized by marginal efficacy. Several studies on the efficacy of antidepressant therapy for major depression have concluded that the treatment of acute disease or maintenance therapy is associated with a 50-60% response rate. (Schulberg et al. (1998) *Arch. Gen. Psychiatry* 55: 1121). The average absolute response rate between antidepressants and placebo is about 20-25%. (Williams et al. (2000) *Ann. Intern. Med.* 132: 743). Consequently, there is a current need for new antidepressant therapies.

In view of the sometimes severe adverse side effects and marginal efficacy of numerous antidepressant therapies, there is a great need for improved pharmaceuticals that effectively treat depressive disorders and sleep disorders without producing the side effects associated with treatments of depression and/or sleep disorders. The present invention provides compositions comprising botulinum toxin neurotoxin for the treatment of depressive and/or sleep disorders as well as other CNS disorders.

The effects of botulinum toxin-based pharmaceuticals for medicinal applications has traditionally been though to act on the peripheral motor and possibly sensory nerves. Such actions of these agents have been used to explain most of the beneficial effects for various indications including movement disorders, pain syndromes, autonomic based syndromes and spastic disorders. To date, clinical observations have been made by the inventor which are indicative of the involvement of the central nervous system and cannot be explained by peripheral effects. Effects on the central nervous system are observed even when botulinum toxin is administered to the scalp, facial or neck regions, including administration by any form of injection except intracranial injection. Such observations include: improvement in photophobia with peri-ocular injections; improvement in sleep patterns and relief of insomnia; improvement of anxiety out of proportion to problems corrected by physical/muscular impairments; improvement in depression out of proportion to problems created by physical/muscular impairment; and effects on dysmenorrheal symptoms and potential effects on gonadotropin hormones or other pituitary hormones.

Additionally, botulinum toxin has been shown to have effects on neurotransmission within the central nervous system when the agent is directly injected into brain parenchyma. Alterations have included depression in electrode depolarization, depression in glutamate release, GABA staining, and cleavage of SNAP-25 in duration consistent with botulinum toxin effect. Intraparenchymal brain injections have been associated with depression of seizure activity within the cerebral hemispheres when seizure provoking scarring is induced by caustic chemical injections. Direct injection into the brain is not practical and in fact unlikely to be conventionally practiced by a physician skilled in the treatment of seizure disorders because of the possibility and risk associated with induced hemorrhage, scarring, neuronal loss and placement difficulty, infection (meningitis) and inconvenience associated with necessary delivery mechanisms. Direct injection into the CNS is highly impractical because of such complications associated with invasive intracranial procedures. Described herein is a system for delivery to the central nervous system (through methods of administration and injection that expressly do not include transcranial, intrathecal or intraspinal injection) of botulinum toxin-based pharmaceuticals, allowing penetration into the central nervous system with enhanced convenience and safety, with fewer or mitigated adverse effects associated with direct delivery.

The present inventors have surprisingly and unexpectedly discovered criteria for the selection of subjects for the treatment of pain syndromes with botulinum toxin. The present invention provides methods for identifying subjects with an increased responsiveness to the treatment of pain with botulinum toxin. Specifically, the inventors have discovered that atopic disease is associated with various pain syndromes, and the presence of atopic disease and relief of pain by tactile stimulation, geste antagoniste phenomenon, seem to have predictive value in forecasting pain response to botulinum toxin.

The application of botulinum toxin for the treatment of myofacial pain initially included tension headaches, bruxism, temporal mandibular joint syndrome, lower-back pain, and post-surgical pain after cervical surgical incisions for the treatment of acoustic neuroma (posterior fossa brain tumor). Application of botulinum toxin for the treatment of migraine headaches became popular after the coincident observation that migraine headaches were relieved after the of botulinum toxin to efface facial wrinkles on the forehead.

Multiple case reports suggest that botulinum toxin is effective for the treatment of tension and migraine headaches, as well as forms of myofacial pain syndrome. Despite this suggestion, controlled trials using small numbers of patients in the study groups, have failed to demonstrate the efficacy of botulinum toxin for the treatment of myofascial and other forms of pain. (Wheeler et al. (1998) A randomized, double-blind, prospective pilot study of botulinum toxin injection for refractory, unilateral, cervicothoracic, paraspinal, myofascial pain syndrome. *Spine* 23(15): 1662-6). The ineffectiveness of botulinum toxin to treat a variety of pain syndromes, in controlled trial, has been attributed to small sample size and relatively low statistical power. The need for larger numbers of patients and further multi-center investigations have been deemed necessary to provide stronger evidence of effectiveness.

In view of case reports suggesting that botulinum toxin is indeed effective for the treatment of migraine-headache-pain syndromes, efforts were made to conduct larger-scale studies. In an initial multi-center controlled study sponsored by the Allergan Pharmaceutical Company, one of the largest suppliers of botulinum toxin A (BOTOX™), efficacy of botulinum toxin to prevent the repetitive occurrence of common migraine headaches (as defined by the International Headache Classification—1988) was suggested. The statistical significance of these results, however, was uncertain, inconsistent between treatment groups, and exhibited unexplained inverted dose response curves. (Silberstein et al. (2000) Botulinum toxin type A as a migraine preventive treatment. *Headache* 40(6): 445-50).

Migraine, tension headaches, myofascial pain of the head, and chronic atypical facial headaches are representative of primary-headache disorders (headaches not associated with structural pathology within the head or not secondary to another disease process). Treatment of these conditions is associated with very high placebo response rates (up to 35%), requiring large numbers of patients to detect significant differences in clinical trials between study and control groups. Utilization of selection criteria (study-induction criteria) that identify a more responsive patient population increases the response rate for subjects within treatment groups of controlled studies, which, in turn, allows a smaller test sample to establish therapeutic efficacy in controlled trials. More importantly, selection criteria (diagnostic criteria) are the basis for accurate and effective medical therapy for any condition. Parameters which identify patients more likely to respond to a given treatment allow: 1) prioritization among therapies when multiple therapeutic options exist; 2) avoidance of therapy unlikely to be successful; and 3) facilitation of informed consent from patients considering risks and benefit ratios. Effective selection criteria assist researchers to further understand mechanisms of action based on clinical evidence.

The present invention provides methods of selecting patients suffering from various pain syndromes, including, but not limited to, myofascial pain, muscle tension headache, and chronic post operative wound syndromes, based on retrospective and prospective analysis in the application of botulinum toxin for the treatment of pain syndromes involving the head and neck.

SUMMARY OF THE INVENTION

The present invention provides methods of treating depressive, anxiety and sleep disorders comprising the administration of pharmaceutical compositions comprising neurotoxins.

The present invention provides methods for treating depression comprising the steps of: a) identifying a subject with a depressive disorder or identifying a subject with one or more symptoms of a depressive disorder; and b) administering an effective amount of a composition comprising a botulinum toxin and a pharmaceutically acceptable carrier to said subject.

The present invention also provides methods of treating anxiety comprising the steps of: a) identifying a subject with an anxiety disorder or identifying a subject with at least one symptom of an anxiety disorder; and b) administering an effective amount of a composition comprising a botulinum toxin and a pharmaceutically acceptable carrier to said subject.

The present invention also provides methods of treating sleep disorders comprising the steps of: a) identifying a subject with a sleep disorder or identifying a subject exhibiting at least one symptom of a sleep disorder; and b) administering an effective amount of a composition comprising a botulinum toxin and a pharmaceutically acceptable carrier to said subject.

The present invention also provides methods of treating circadian rhythm disorders comprising the steps of: a) identifying a subject with a circadian rhythm disorder; and b) administering an effective amount of a composition comprising a botulinum toxin and a pharmaceutically acceptable carrier to said subject.

The present invention also provides methods of delivering botulinum toxin across a blood-brain barrier comprising the steps of: a) identifying a subject with at least one neuropsychiatric disorder; and b) administering a composition comprising a neurotoxin and a pharmaceutically acceptable carrier to said subject in an amount sufficient to deliver said neurotoxin across the blood-brain barrier.

The present invention also provides methods of delivering botulinum toxin across a blood-brain barrier comprising the steps of: a) identifying a subject with at least one neuropsychiatric disorder; and b) administering a composition comprising a neurotoxin and a pharmaceutically acceptable carrier to said subject in an amount sufficient to deliver said neurotoxin across the blood-brain barrier, wherein said administration of said injection of neurotoxin blocks at least one neurotransmitter. In a preferred embodiment, the neurotransmitter is acetylcholine.

The present invention also provides methods of treating an anxiety disorder comprising the steps of: a) identifying a subject with at least one anxiety disorder or identifying a subject with one or more symptoms of an anxiety disorder; and b) administering to said subject a composition comprising a neurotoxin and a pharmaceutically acceptable carrier said composition is delivered across the blood-brain barrier in an amount sufficient to decrease cholinergic neuron transmission.

The present invention also provides methods of treating a sleep disorder comprising the steps of: a) identifying a subject with at least one sleep disorder or identifying a subject with one or more symptoms of a sleep disorder; and b) administering to said subject a composition comprising a neurotoxin and a pharmaceutically acceptable carrier said composition is delivered across the blood-brain barrier in an amount sufficient to decrease cholinergic neuron transmission. In a preferred embodiment, the composition decreases choline acetyltransferase activity. In another preferred embodiment, the composition decreases the synthesis of acetylcholine. In another preferred embodiment, the sleep disorder is insomnia. In another preferred embodiment, the sleep disorder is narcolepsy, restless leg syndrome or sleep apnea.

The present invention also provides methods of treating a circadian rhythm disorder comprising the steps of: a) identifying a subject with at least one circadian rhythm disorder or identifying a subject with one or more symptoms of a circadian rhythm disorder; and b) administering to said subject a composition comprising a neurotoxin and a pharmaceutically acceptable carrier said composition is delivered across the blood-brain barrier in an amount sufficient to decrease cholinergic neuron transmission. In a preferred embodiment, the composition decreases choline acetyltransferase activity. In another preferred embodiment, the composition decreases the synthesis of acetylcholine.

The present invention also provides methods of treating a depressive disorder comprising the steps of: a) identifying a subject with at least one depressive disorder or identifying a subject with one or more symptoms of a depressive disorder; and b) administering to said subject a composition comprising a neurotoxin and a pharmaceutically acceptable carrier said composition is delivered across the blood-brain barrier in an amount sufficient to decrease cholinergic neuron transmission. In a preferred embodiment, the composition decreases choline acetyltransferase activity. In another preferred embodiment, the composition decreases the synthesis of acetylcholine.

The present invention provides methods of selecting a subject for the treatment of pain with botulinum toxin, comprising the step of identifying a subject suffering from a pain syndrome and a condition selected from the group consisting of a depressive disorder, an anxiety disorder and a sleep disorder, wherein the identification of a subject with a pain syndrome and a condition selected from the group consisting of a depressive disorder, an anxiety disorder and a sleep disorder is predictive of increased responsiveness to the treatment of pain with botulinum toxin. In a preferred embodiment, the pain syndrome is any one or a combination of the pain syndromes selected from the group consisting of: myofacial pain; migraine headache; post operative would pain; sinusitis-related headaches; muscle tension headaches; post-traumatic headaches; cluster headaches; temporal mandibular joint syndrome; fibromyalgia; atypical facial pain; post incisional wound pain; cervical radiculopathy; and whiplash.

In another embodiment of the present invention, subjects suffering from a condition selected from the group consisting of a depressive disorder, an anxiety disorder and a sleep disorder were identified by determining that a subject has a medical history of a depressive disorder, an anxiety disorder, or a sleep disorder, respectively.

The present invention also provides methods of identifying a subject with increased responsiveness to treating a pain disorder with botulinum toxin, comprising the step of screening a population of subjects to identify those subjects that suffer from a pain disorder and a condition selected from the group consisting of a depressive disorder, an anxiety disorder and a sleep disorder, wherein the identification of a subject with a pain syndrome and a condition selected from the group consisting of a depressive disorder, an anxiety disorder and a sleep disorder is predictive of increased responsiveness to the treatment of pain with botulinum toxin. In a preferred embodiment, the pain syndrome is any one or a combination of the pain syndromes selected from the group consisting of: myofacial pain; migraine headache; post operative would pain; sinusitis-related headaches; muscle tension headaches; post-traumatic headaches; cluster headaches; temporal mandibular joint syndrome; fibromyalgia; atypical facial pain; post incisional wound pain; cervical radiculopathy; and whiplash.

The present invention provides a method that comprises the steps of identifying or diagnosing a pain syndrome; diagnosing or eliciting a history of a condition selected from the group consisting of a depressive disorder, an anxiety disorder and a sleep disorder; and classifying the identified pain syndrome as one with increased responsiveness to treatment with botulinum toxin. In one embodiment, a pain syndrome is identified according to the International Headache Classification System (The International Headache Society (I.H.S.)).

The present invention provides a method of selecting patients for the treatment of human headache disorders with a botulinum toxin based pharmaceutical, comprising diagnosing headache type occurring in a patient suffering from a depressive disorder, an anxiety disorder, obsessive compulsive behavioral traits, or a sleep disorder and administering a therapeutically effective amount of botulinum toxin. In one embodiment the headache disorder is migraine, tension headache, combined tension and migraine headache, myofascial headache, sinus headache, headache associated with temporal mandibular joint syndrome, headache associated with fibromyalgia, or headache associated with neuralgia.

The present invention also provides a method of selecting patients for the treatment of human facial pain disorders with a botulinum toxin based pharmaceutical, comprising diagnosing a facial pain disorder occurring in a patient suffering from a depressive disorder, an anxiety disorder, obsessive compulsive behavioral traits, or a sleep disorder and administering a therapeutically effective amount of botulinum toxin. In one embodiment, the facial pain disorder is trigeminal neuralgia, the facial pain disorder is associated with bruxism, or the facial pain disorder is post operative chronic surgical wound pain.

The compositions of the present invention comprise botulinum toxin and a pharmaceutically acceptable carrier. In a preferred embodiment, the botulinum toxin is immunotype A, B, C, D, E, F, or G. In a more preferred embodiment, the botulinum toxin is botulinum toxin type A from Hall strain *Clostridium botulinum*.

The methods of the present invention may preferably be practiced by administering the botulinum toxin compositions by injection, including transcutaneous, percutaneous, subcutaneous, intraperitoneal, transdermal, intramuscular and intraosseous, but expressly not intracranial, transcranial, intrathecal or intraspinal injection or administration. In one embodiment, there are at least two injection sites. In another embodiment, the injections are multifocal. The botulinum toxin may be preferably administered to the forehead, scalp or neck or other locations such as the periocular region and other areas of the face that enhance maximize venous drainage from the site of administration to the central nervous system (CNS). In another embodiment, the botulinum toxin may be administered to the soft tissues outside the neurocranium. In another embodiment, the botulinum toxin may be administered in locations that maximize uptake by the portal hypophyseal drainage.

Examples of compounds and formulations which can be used in the present invention include botulinum toxin stabilized with a protein such as serum albumin or hyaluronidase. In a preferred embodiment the serum albumin or hyaluronidase is recombinant. In another embodiment, the serum albumin is present at a concentration of greater than 500 μg/100 $LD_{50}$ units botulinum toxin. The botulinum toxin pharmaceutical may be further stabilized with a simple stabilizing sugar or polysaccharide (e.g. sucrose, lactose or trehalose). The botulinum toxin is preferably a monocomponent neurotoxin of a molecular weight of 150,000 daltons that is free of complex botulinum toxin proteins. The compositions disclosed herein may also comprise a polyethylene glycol polymer; a vegetable fat-based nanoemulsion; and any nanoemulsion using one or more monounsaturated or polyunsaturated oils. In a preferred embodiment, the botulinum toxin compositions used in the methods of the present invention are formulated to enhance penetration of the botulinum toxin into and through the skin.

Recent advances in pharmaceutical technology have focused on enhanced delivery systems such as transdermal or transcutaneous delivery systems. Such systems are thought to be more convenient and associated with less pain. The problems associated with such systems include poor penetration of materials through the epidermis and dermis. Hyaluronidase offers improved penetration.

A pharmaceutical composition comprising botulinum neurotoxin, hyaluronidase, and sugars (both simple and oligosaccharides) is suitable for the methods of the present invention. The botulinum toxin pharmaceutical formulations suitable for use in for the methods of the present invention are preferably devoid of any human blood or recombinant blood products and will be either stabilized in flash or freeze dried form. The pH is preferably between pH 3.0 to 7.4 and the preparation may be used as an injection, transdermal or topical agent. The botulinum toxin pharmaceutical formulations suitable for use in for the methods of the present invention may be administered by injection, needleless delivery systems and methods requiring disruption techniques such as electroporation, sonication, and high pressure air gas flow injection or in the form of a micro-needle. Micro-needles are generally from 150 to 600 microns. Furthermore, the botulinum toxin pharmaceutical formulations suitable for use in for the methods of the present invention may further comprise polycationic proteins.

Currently, hyaluronidase is available at a number of specific activities. For example, sheep based materials can have a specific activity of 1,500 Upper mg or 1.5 Upper mcg. Typically, 75-300 U are used for injection, such as conducted with peri-bulbar anesthesia for intra-ocular surgery. This would correspond to about 100-450 mg in mass of enzymatic protein, enough to act as a stabilizing excipient.

Prior studies have show that a protein excipient, such as human serum albumin, can stabilize the botulinum toxin. Test studies conducted demonstrate that hyaluronidase also stabilizes the botulinum toxin at the same levels observed for the human serum albumin.

The compositions disclosed herein may be such that the doses are formulated into a concentration suitable for administration as an eye drop to facilitate transconjunctival penetration for the treatment of ocular surface diseases. The compositions disclosed herein may be such that the $LD_{50}$ units range from 1.25U-3,000 units of botulinum toxin type A. The compositions disclosed herein may be such that the $LD_{50}$ units range from 1.25-20,000 U of botulinum type B. The compositions disclosed herein may be such that the formulation is delivered into the nose or oral cavity as an aerosol to facilitate intracranial delivery of a botulinum toxin based pharmaceutical. The compositions disclosed herein may be such that the formulation is delivered into the ear canal as an aerosol to facilitate intracranial delivery of a botulinum based pharmaceutical The present invention provides methods for delivering a botulinum toxin based pharmaceutical to the central nervous system of a subject by any injection or topical application method, except intracranial, transcranial, intrathecal or intraspinal injection, in a therapeutically effective amount sufficient to decrease at least one central nervous system neurotransmitter when compared to an untreated subject. In a preferred embodiment, the at least one central nervous system neurotransmitter is glutamate, norepinephrine, or acetyl-choline. In a more preferred embodiment, the at least one central nervous system neurotransmitter is glutamate. In another embodiment, the methods of the present invention decrease at least one central nervous system neurotransmitter when compared to an untreated subject sufficiently to reduce at least one symptom of insomnia, a sleep disorder, an anxiety disorder, a depressive disorder, dysmenorrhea, an appetite or eating disorder, or a seizure disorder. In a preferred embodiment the seizure disorder is generalized, focal motor, or partial complex.

Glutamate is a neurotransmitter that exhibits endogenous neurotoxic activity that is observed in a number of neurodegenerative diseases and disorders, vascular accidents such as stroke and in seizure disorders. For example, subjects with mild to moderate dementia and probable Alzheimer's Disease have been shown to exhibit elevated levels of glutamate in the central nervous system. Elevated glutamate in the central nervous system is reflective of increased glutamatergic activity in the early stages of Alzheimer's Disease. The progressive neuronal loss observed in Alzheimer's Disease and other neurodegenerative disorders and diseases correlate with elevated glutamate and the increased excitotoxicity associated with elevated levels of this neurotransmitter.

The present invention provides methods for reducing glutamate levels in the central nervous system, the brain or portions of the brain comprising the step of administering a botulinum toxin pharmaceutical to a subject, by any injection or topical application method, except intracranial, transcranial, intrathecal or intraspinal injection, in an amount sufficient to reduce glutamate levels in the central nervous system, the brain or portions of the brain compared to an untreated subject.

The present invention provides methods for neuroprotection comprising the step of administering a botulinum toxin pharmaceutical to a subject, by any injection or topical application method, except intracranial, transcranial, intrathecal or intraspinal injection, in an amount sufficient to reduce neuronal loss in the central nervous system, the brain or portions of the brain compared to an untreated subject.

The present invention also provides methods for delivering a botulinum toxin based pharmaceutical to the central nervous system of a subject by injection into the nasal sinuses in a therapeutically effective amount sufficient to decrease at least one central nervous system neurotransmitter when compared to an untreated subject. In a preferred embodiment, the at least one central nervous system neurotransmitter is glutamate, norepinephrine, or acetyl-choline. In a more preferred embodiment, the at least one central nervous system neurotransmitter is glutamate. In another embodiment, the methods of the present invention decrease at least one central nervous system neurotransmitter when compared to an untreated subject sufficiently to reduce at least one symptom of insomnia, a sleep disorder, an anxiety disorder, a depressive disorder, dysmenorrhea, or a seizure disorder. In a preferred embodiment the seizure disorder is generalized, focal motor, or partial complex.

The present invention also provides methods for delivering a botulinum toxin based pharmaceutical to the central nervous system of a subject by any injection or topical application method, except intracranial, transcranial, intrathecal or intraspinal injection, in a therapeutically effective amount sufficient to decrease at least one central nervous system neurotransmitter when compared to an untreated subject. In a preferred embodiment, the at least one central nervous system neurotransmitter is glutamate, nor-epinephrine, or acetyl-choline. In a more preferred embodiment, the at least one central nervous system neurotransmitter is glutamate. In another embodiment, the methods of the present invention decrease at least one central nervous system neurotransmitter when compared to an untreated subject sufficiently to reduce an agitated behavior associated with mental retardation, schizophrenia, Huntington's Chorea or Alzheimer's Disease.

The present invention also provides methods for delivering a botulinum toxin based pharmaceutical to the central nervous system of a subject by any injection or topical application method, except intracranial, transcranial, intrathecal or intraspinal injection, in a therapeutically effective amount sufficient to decrease at least one central nervous system neurotransmitter when compared to an untreated subject. In a preferred embodiment, the at least one central nervous system neurotransmitter is glutamate, nor-epinephrine, or acetyl-choline. In a more preferred embodiment, the at least one central nervous system neurotransmitter is glutamate. In another embodiment, the methods of the present invention decrease at least one central nervous system neurotransmitter when compared to an untreated subject sufficiently to reduce at least one symptom of a neurodegenerative disease associated with inflammation.

The present invention also provides for the use of botulinum toxin or a botulinum toxin composition of the present invention in the production of a medicament for the treatment of any one of the disorders, diseases or conditions disclosed herein, including depressive disorders, anxiety disorders, sleep disorders, circadian rhythm disorders, neuropsychiatric disorders, Alzheimer's Disease and the like, and for the treatment of pain, such as various headache pain, associated with a pain syndrome.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depicts the decreased glutamate receptor activity in the neostriatum of a botulinum-toxin-treated mouse as compared to an untreated mouse.

DETAILED DESCRIPTION OF THE INVENTION

A. Definitions

As used herein, "administration" of a composition means any route of administration, including but not limited to oral, nasal, transcutaneous, percutaneous, subcutaneous, intraperitoneal, transdermal, intramuscular and intraosseous, but expressly excludes administered by any method, except intracranial, transcranial, intrathecal or intraspinal injection.

As used herein, "Botulinum toxin" means a protein toxin and its complexes isolated from strains of *Clostridium botulinum*, including various immunotypes such as A, B, C1, C2, C3, D, E, F and G.

As used herein, "depressive disorder" means major depression, dysthymia, and atypical depression or depression not otherwise specified.

As used herein, "an effective amount" is an amount sufficient to reduce one or more symptoms associated with a depressive, anxiety or sleep disorder or any of the disorders described herein.

As used herein, the term "pharmaceutically acceptable carrier" means a chemical composition with which the active ingredient may be combined and which, following the combination, can be used to administer the active ingredient to a subject. "Pharmaceutically acceptable carrier" also includes, but is not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

As used herein, "increased responsiveness" refers to an increase in the ratio of subjects responsive to pain treatment with botulinum toxin to total subjects (responsive and unresponsive to botulinum toxin).

As used herein, "response ratio" refers to the ratio of subjects responsive to pain treatment with botulinum toxin to total subjects (responsive and unresponsive to botulinum toxin).

As used herein, the term "screening a population" means a retrospective review and analysis of the medical history of a subject or an identification of a specific contemporaneous diagnosis.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In addition to the active ingredient, a pharmaceutical composition of the invention may further comprise one or more additional pharmaceutically active agents. Particularly contemplated additional agents include antiemetics and scavengers such as cyanide and cyanate scavengers. Controlled- or sustained-release formulations of a pharmaceutical composition of the invention may be made using conventional technology.

As used herein, the term "physiologically acceptable" ester or salt means an ester or salt form of the active ingredient which is compatible with any other ingredients of the pharmaceutical composition, which is not deleterious to the subject to which the composition is to be administered.

B. Depressive Disorders

Depressive disorders encompass the diagnoses of major depression, dysthymia, and atypical depression or depression not otherwise specified ("minor depression"). The different subgroups of depressive disorders are categorized and defined by the Diagnostic and Statistical Manual of Mental Disorders, Fourth Edition (DSM-IV). (American Psychiatric Association. Diagnostic and Statistical Manual of Mental Disorders, $4^{th}$ Ed., Primary Care Version (DSM-IV-PC). American Psychiatric Association Press, Washington, D.C. 1995). According to the DSM-IV, a diagnosis of "major depression" requires that a patient present with at least five of the following nine symptoms during the diagnostic period: 1) depressed mood most of the day (most acute in the morning); 2) markedly diminished interest or pleasure in nearly all activities (anhedonia); 3) significant weight loss or gain; 4) insomnia or hypersomnia; 5) psychomotor agitation or retardation; 6) fatigue or energy loss; 7) feelings of guilt and worthlessness; 8) impaired concentration and indecisiveness; and 9) recurring thoughts of death or suicide. To support a diagnosis of major depression, a depressed mood or loss of interest (anhedonia) must be one of the five observed symptoms. In contrast, a diagnosis of "atypical depression" or "depression not otherwise specified" (also referred to as "minor depression"), the most common form of depression, requires between 2 and 4 depressive symptoms that are present daily or for most of the day for at least a two week period. Dysthymia is a chronic, low intensity mood disorder characterized by anhedonia, low self esteem and low energy that persists for more than two years, consecutively. Seasonal affective disorder is considered to be a form of major depression characterized by seasonal variation.

Depressive disorders do not include normal emotional reactions, a normal grief reaction or reactions secondary to an organic cause such as a physical illness or drug exposure. As used herein, depressive disorders refer to primary disorders of mood and sleep patterns and not secondary or reaction disorders. Such reactionary disorders occur secondarily to other medical disorders such as hyperhydrosis, cervical dystonia, migraine headache, tension headaches, various pain syndromes, jaw spasms, blepharospasm, strabismus, inflammatory local and systemic diseases, post operative pain syndromes, hemifacial spasms, cancer, myocardial infarction, stroke, degenerative neurological diseases, or any other physical ailment causing an emotional reaction.

C. Anxiety

Anxiety is a group of disorders characterized by a number of both mental and physical symptoms, with no apparent explanation. Apprehension, fear of losing control, fear of going "crazy", fear of pending death, impending danger, or uneasiness are among the most common mental symptoms. Common physical symptoms include dizziness, lightheadedness, chest pain, abdominal pain, nausea, increased hear rates or diarrhea. Chronic anxiety, also referred to as Generalized Anxiety Disorder, manifests as persistent worries, fears, and negative thoughts lasting a minimum of six months. Chronic anxiety often results in excessive worry over daily activities, headaches and nausea. Sleep disorders or early awakening, depression, tension, muscle aches and fatigue can all accompany chronic anxiety.

Acute anxiety, or Panic Disorder, comes on as a sudden attack or fear accompanied by symptoms that may resemble a heart attack, such as palpitations, chest pain and dizziness. Shortness of breath, stomach upset, chills, cold sweats, hot flashes, or irrational fears of death can combine with these symptoms to create a terrifying experience for the individual experiencing them. Excessive levels of nor epinephrine are seen to increase the rates of breathing and pulse in panic attack sufferers. Post-traumatic Stress Disorder is also classed as an anxiety disorder, and can be triggered by anyone experiencing or witnessing a deeply traumatic event. Some symptoms of Post-Traumatic Stress Disorder can be anger, depression, emotional numbness, flashbacks, nightmares and a tendency to startle easily.

Phobias, or irrational fears, and Obsessive Compulsive Disorder, a tendency towards repetitive or uncontrollable behavior, are also classed with anxiety disorders. These may co-exist together, as many individuals with obsessive compulsive disorder have phobias of germs or lack of cleanliness and may was their hands or bathe excessively.

Anxiety disorders do not include normal emotional reactions, a normal reaction to stress or reactions secondary to an organic cause such as a physical illness or drug exposure.

D. Sleep Disorders

Circadian rhythm describes the approximately 24-hour cycles that are generated by an organism. Most physiological systems demonstrate circadian variations. The systems with the most prominent variations are the sleep-wake cycle, thermoregulation, and the endocrine system. Circadian rhythm disturbances can be categorized into two main groups: transient disorders (e.g., jet lag, altered sleep schedule due to work, social responsibilities, illness) and chronic disorders. The most common chronic disorders are delayed sleep-phase syndrome (DSPS), advanced sleep-phase syndrome (ASPS), and irregular sleep-wake cycle. Katzenberg et al. have suggested a genetic correlation (i.e., clock polymorphisms) to circadian rhythm patterns. DSPS is characterized by a persistent inability (more than 6 mo) to fall asleep and awaken at socially accepted times. Once asleep, these patients are able to maintain their sleep and have normal total sleep times. (In contrast, patients with insomnia have a lower than normal total sleep time, due to difficulties in initiating or maintaining sleep.) ASPS is characterized by persistent early evening sleep onset (between 6:00 and 9:00 pm) with an early morning wake-up time, generally between 3:00 and 5:00 am. ASPS occurs much less frequently than DSPS and is seen most commonly in the elderly and in individuals who are depressed.

The neural basis of the circadian rhythm, the suprachiasmatic nuclei (SCN), is located in the anterior ventral hypothalamus and has been identified as the substrate that generates circadian activity. Lesions of the SCN produce loss of circadian rhythmicity of the sleep-wake cycle, the activity-rest cycle, skin temperature, and corticosteroid secretion. Other pacemakers exist that are not located in the SCN. For instance, core body temperature rhythm persists in spite of bilateral ablation of SCN. Furthermore, free-running studies have provided evidence for multiple circadian oscillators. Under free-running conditions, circadian rhythm may split into independent components.

The SCN are the site of the master circadian clock in mammals. The SCN clock is mainly entrained by the light-dark cycle. Light information is conveyed from the retina to the SCN through direct, retinohypothalamic fibers. The SCN also receive other projections, like cholinergic fibers from basal forebrain. Cholinergic afferents and transmission have been shown to be involved in regulation of light-induced circadian rhythms. (Erhardt et al. 2004 The Neuroanantomy of the Circadian Rhythm.).

In the United States, DSPS is common. Approximately 7-10% of patients who complain of insomnia are diagnosed with a circadian rhythm disorder, most often DSPS. The prevalence of DSPS is probably higher than that because the total sleep time is typically normal in patients with DSPS and because patients with DSPS adjust their lifestyle to accommodate their sleep schedule and do not seek medical treatment. In adolescence, the prevalence is approximately 7%. In contrast, true ASPS probably is quite rare. An age-related phase advance, however, is common in the elderly, who tend to go to sleep early and get up early.

The diagnosis of circadian rhythm disorders is based primarily on a thorough social, physical and neurological history. Differentiation of transient disorders from chronic disorders and primary disorders from secondary disorders influences the direction of evaluation and treatment plans. As with all medical and psychiatric histories, the nature of the complaint is the first order of business. In cases of sleeplessness, distinguishing individuals with difficulty initiating sleep from those with difficulty maintaining sleep, those with significant daytime impairment, and those complaining of nonrestorative sleep is important.

Disorders associated with various sleep disorders include narcolepsy, cataplexy, restless-leg syndrome, and sleep apnea. Anxiety disorders do not include normal emotional reactions, a normal reaction to stress or reactions secondary to an organic cause such as a physical illness or drug exposure.

E. CNS Disorders

The present invention is also directed to methods of using botulinum toxin based pharmaceuticals injected transcutaneously or by any of the routes of administration disclosed herein, to induce a central nervous system depressive effect for the treatment of various CNS disorders. The inventor has found that botulinum toxin exerts a CNS depressive effect in rats injected transcutaneously in the scalp. The injections are not intracranial or directly into the brain, but may include or specifically exclude intrathecal and intraspinal injection or administration. It is hypothesized that transcutaneous administration of botulinum toxin penetrates the blood/brain barrier. The present invention provides methods for using the botulinum toxin based pharmaceuticals disclosed herein for the treatment of seizures, anxiety, agitation, mania, bipolar disorders, generalized seizures, mental retardation, delirium, hyperactivity syndrome, attention deficit disorder (ADD), dementia, Huntington's disease, Alzheimer's disease, Parkinson's disease, psychosis, schizophrenia, insomnia and other CNS disorders.

In certain embodiments, the botulinum toxin based pharmaceuticals disclosed herein are used at various dosage levels to induce a generalized atrophic effect in the CNS. This effect is useful in the treatment of various CNS disorders. The inventor has found that rats injected with high doses of botulinum toxin (i.e. doses at or near the $LD_{50}$) exhibit expanded or enlarged lateral ventricles in their brains. Controls show no such effects while treated animals show a marked effect. Generalized brain atrophy is indicative of biological activity at the level of neurotransmitters that is induced by transcutaneous administration of botulinum toxin. The evidence is consistent with a suppressive effect in the hypothalamus in the treated animals. This could cause direct effects on the release of hormones such as thyroid releasing factors, gonadotropin releasing factor, etc.

All books, articles, patents or other publications and references are hereby incorporated by reference in their entireties. Reference to any compound herein includes the racemate as well as the single enantiomers.

EXAMPLES

The following Examples serve to further illustrate the present invention and are not to be construed as limiting its scope in any way.

Example 1

A 78-year-old male who noted sleep disturbances and anxiety was initially diagnosed with blepharospasm. Botulinum toxin was administered by injection, and the subject noted improved sleep and reduced anxiety.

Example 2

A 44-year-old bus driver was diagnosed with hemifacial spasm and reported symptoms of anxiety. Botulinum toxin was administered by injection. The subject noted a better ability to cope with work-related stresses and cope with difficult situations with less stress.

Example 3

A 72-year-old consultant diagnosed with hemifacial spasm who reported sleep disturbances and anxiety was treated with botulinum toxin that was administered by injection. The subject reported improved sleep and reduced anxiety and less agitation.

Example 4

A 45-year-old woman was treated for cosmetic indications with botulinum toxin. The initial diagnosis was cosmetic rhytides. The subject noted fewer symptoms of depression and less anxiety for a period of two months.

Example 5

A 44-year-old woman diagnosed with severe tension headaches and sleep disturbances was treated with botulinum toxin by injection. The subject noted improved sleep patterns and fewer headaches up to two months after treatment.

Example 6

A 73-year-old male with essential blepharospasm reported sleep disturbances and anxiety characterized as "nervous tension." Botulinum toxin was administered by injection. The subject noted less anxiety and improved sleep after the injections. The reduced symptoms lasted two to three months and ultimately recurred.

Example 7

A 43-year-old person with myofacial pain and sleep problems was treated with botulinum toxin by injection. The subject noted better sleep patterns after injections that lasted three months.

Example 8

A 42-year-old person was diagnosed with myofacial pain, tension headaches and depression and treated with botulinum toxin administered by injection. The subject noted some improvement in sleep pattern after the toxin injections.

Example 9

The subject is a 54-year-old person diagnosed with essential blepharospasm and depression. Botulinum toxin was introduced by injection. The subject noted fewer symptoms of depression after the botulinum toxin injections.

Example 10

The subject is a 57-year-old physician diagnosed with essential blepharospasm. Botulinum toxin was introduced by injection. The subject noted a feeling of euphoria, well being and improved mood after the botulinum toxin injections.

Example 11

A 47 year old woman with a history of cervicogenic headache and frequent problems of insomnia. The insomnia was characterized by difficulty initiating sleep, intermittent awakening, early-morning awakening, and inability to maintain sleep. Injections were given in the regions generally used to treat spasmodic torticollis as well as in multiple locations along the hairline, both anterior and posterior. Doses ranged between 5-20 units per subcutaneous injection site with a total dose of 100 U. Within 3-5 days, improvement in the insomnia occurred and lasted between 10-14 weeks. Improvement in each component of her sleep disorder occurred. Recurrence of the sleep disorder occurred after the 10-14 week period.

Example 12

A 52 year old woman received botulinum injections for the effacement of glabellar rhytides (facial wrinkles). Further injections were given in multiple locations along the hairlines, she also suffered from insomnia with difficulty initiating sleep and sustaining sleep. After injection with botulinum toxin, sleep pattern improved and lasted the duration of about 10-12 weeks. Total dose administered in multiple locations was 30 Units.

Example 13

A 71 year old man with essential blepharospasm was injected with 60 U divided along the peri-ocular region and the forehead. Improvement in sleep pattern characterized by more continuous sleep was noted after each injection. The benefit lasted about 3 months and has been noted over 3 injection cycles. When brought to the patient's attention, he associated the improvement to the botulinum toxin injections. Insomnia recurred when he felt the time for repeat injection with botulinum toxin.

Example 14

A botulinum toxin composition is prepared from any immunotype (A-G) consisting of monocomponent neurotoxin molecules free of accessory or complex proteins, containing human serum albumin, and a nanoemulsion, with various charges. The nanoemulsion may contain polymers consisting of any of the following: polyethylene glycol, vegetable oil, a vegetable oil derivative or a monounsaturated or polyunsaturated oil. The pH may be altered in the preparation to enhance permeability. Alternatively, botulinum toxin is prepared from immunotypes A-G consisting of a monocomponent neurotoxin, without a nanoemulsion carrier, albumin and an acidic pH between 1-6 units. The effect on the central nervous system from transcutaneous injection was demonstrated using a rodent animal model typically used for research in neurodegenerative disease (20-30 gram mice). Injections were given over the scalp region with botulinum type A toxin at a dose close and approximating the $LD_{50}$ for this animal. Surviving animals were subjected to autopsy and serial brain cutting and histologically stained using a standard Nissle formula. Substantial atrophy of basal ganglion and periventriclular cells was noted. Such changes are not usually seen with systemic illness without direct brain pathology. The neuropathologic assessment is that direct suppressant effects do occur within the central nervous system at high dose (close to the $LD_{50}$ for the animal model). More subtle changes are anticipated and seen at lower therapeutic doses based on clinical observations of efficacy for insomnia, dysmenorrhea, depression and anxiety. The experimentation described herein indicates blockage of neurotransmission usually of excitatory neurotransmitters to the extent that pathologic change occurs in brain structures. The major central nervous system neuroransmitters blocked include glutamate, norepinephrine, acetylcholine. GABA effects are augmented. SNAP-25 is noted to be cleaved throughout the targeted areas.

Example 15

The effect on the central nervous system from transcutaneous injection was demonstrated using a rodent animal model typically used for research in neurodegenerative disease (20-30 gram mice). Four injections of botulinum toxin (totaling 0.8 $LD_{50}$ units) were given over the scalp region. Surviving animals were subjected to autopsy and serial brain cutting and histologically stained using a standard Nissle formula. Substantial atrophy of basal ganglion and periventriclular cells was noted. Substantial decrease of cholinergic neurons was noted. Substantial decrease in the amount of choline acetyltransferase was noted. More subtle changes are anticipated at lower therapeutic doses based on clinical observations of efficacy for insomnia, dysmenorrhea, depression and anxiety. The experimentation described herein demonstrates blockage of neurotransmission usually of excitatory neurotransmitters to the extent that pathologic change occurs in brain structures. The major central nervous system neuroransmitters blocked include glutamate, norepinephrine, and acetylcholine. GABA effects are augmented. SNAP-25 is noted to be cleaved throughout the targeted areas.

Example 16

The effect on the central nervous system from transcutaneous injection was demonstrated using a rodent animal model typically used for research in neurodegenerative disease (20-30 gram mice). Four injections of botulinum toxin (totaling 0.8 $LD_{50}$ units) were given over the scalp region. Surviving animals were subjected to autopsy and serial brain cutting and histologically stained using a standard Nissle formula. Serial cut mouse tissue sections were stained for Nissle substance using cresyl violet and immunostained for glutamate receptor activity. Sections were rinsed in TRIS-buffered saline with Tween 20 (TBS-T) containing 10% normal goat serum for one hour. Sections were then incubated overnight in TBS-T with 0.1% sodium azide and anti-GluR4. Sections were rinsed three times in TBS-T, followed by a 2-3 hour incubation in TBS-T containing a goat anti-mouse peroxidase-conjugated secondary antibody to detect glutamate. Sections were then rinsed three times in TBS-T. Antibody complexes were visualized using diaminobenzidine. Preabsorbtion with excess target protein, or omission of either primary or secondary antibody, were used to demonstrate antibody specificity and background generated from the detection assay. Tissue sections were examined using a Nikon Eclipse E800 microscope with a Spot RT digital camera. Photographs of tissue sections of neostriatum in an untreated mouse (sham injection) and a botulinum toxin treated mouse (four injections totaling 0.8 $LD_{50}$ BOTOX® injected transdermally over the scalp reason) shown in FIG. 1.

I claim:

1. A method of treating sleep onset insomnia or sleep maintenance insomnia comprising the steps of:
    a) identifying a subject with said sleep disorder; and
    b) administering an effective amount of a composition comprising a botulinum toxin immunotype A and a pharmaceutically acceptable carrier to said subject thereby reducing at least one symptom of said sleep disorder.

2. The method of claim 1, wherein the botulinum toxin is botulinum toxin type A from Hall strain *Clostridium botulinum*.

3. The method of claim 1, wherein the composition is administered by injection.

4. The method of claim 3, wherein the injection is multifocal.

5. The method of claim 3, wherein the composition is administered to the forehead.

6. The method of claim 3, wherein the composition is administered to the scalp.

7. The method of claim 3, wherein the composition is administered to the neck.

8. The method of claim 1, wherein there are at least two injection sites.

9. The method of claim 1, wherein the composition is administered transdermally.

10. A method of treating sleep onset insomnia or sleep maintenance insomnia comprising the steps of:
    a) identifying a subject with said sleep disorder;
    b) administering to said subject a composition comprising a botulinum toxin immunotype A and a pharmaceutically acceptable carrier by injection.

11. The method of claim 10, wherein said composition decreases choline acetyltransferase activity.

12. The method of claim 10, wherein said composition decreases synthesis of acetylcholine.

13. The method of claim 10, wherein said botulinum toxin immunotype A is of the Hall strain.

14. The method of claim 10, wherein injection is transcutaneous, subcutaneous, transdermal, or intramuscular.

15. The method of claim 14, wherein the injection is multifocal.

16. The method of claim 14, wherein the composition is administered to the brow or forehead.

17. The method of claim 14, wherein the composition is administered to the scalp.

18. The method of claim 14, wherein the composition is administered to the neck.

19. The method of claim 10, wherein the composition is administered transdermally.

* * * * *